US008383851B2

(12) United States Patent
Botts et al.

(10) Patent No.: US 8,383,851 B2
(45) Date of Patent: Feb. 26, 2013

(54) LACTYLATE SYNTHESIS METHODS USING DILACTIDES

(75) Inventors: Jeff B. Botts, Overland Park, KS (US); Margaret Walsh, Mission, KS (US)

(73) Assignee: Caravan Ingredients Inc., Lenexa, KS (US)

( * ) Notice: Subject to any disclaimer, the term of this patent is extended or adjusted under 35 U.S.C. 154(b) by 46 days.

(21) Appl. No.: 12/882,921

(22) Filed: Sep. 15, 2010

(65) Prior Publication Data

US 2012/0065422 A1   Mar. 15, 2012

(51) Int. Cl.
*C07C 69/66*   (2006.01)
*C07D 319/12*   (2006.01)
(52) U.S. Cl. .................. 560/185; 560/179; 549/379
(58) Field of Classification Search .................. None
See application file for complete search history.

(56) References Cited

U.S. PATENT DOCUMENTS

| | | | |
|---|---|---|---|
| 2,350,388 A | 6/1944 | Claborn et al. | |
| 2,733,252 A | 1/1956 | Thompson et al. | |
| 2,744,825 A | 5/1956 | Thompson et al. | |
| 2,789,992 A | 4/1957 | Thompson et al. | |
| 3,141,030 A | 7/1964 | Buddemeyer et al. | |
| 3,728,447 A | 4/1973 | Osipow et al. | |
| 3,855,149 A | 12/1974 | Bielskis | |
| 3,865,855 A | 2/1975 | Linn et al. | |
| 3,870,799 A | 3/1975 | Tenney | |
| 3,883,669 A | 5/1975 | Tsen et al. | |
| 3,933,825 A | 1/1976 | Fiscella et al. | |
| 4,146,548 A | 3/1979 | Forsythe | |
| 4,164,593 A | 8/1979 | Marnett et al. | |
| 4,184,978 A | 1/1980 | France et al. | |
| 4,198,311 A | 4/1980 | France et al. | |
| 4,766,167 A | 8/1988 | Marnett et al. | |
| 4,865,869 A | 9/1989 | Tenney et al. | |
| 5,000,974 A | 3/1991 | Albersmann | |
| 5,002,780 A | 3/1991 | Bakta et al. | |
| 5,274,127 A * | 12/1993 | Sinclair et al. ............... 549/274 |
| 5,686,630 A * | 11/1997 | Miao et al. ............... 549/274 |
| 6,025,006 A | 2/2000 | Miller et al. | |
| 6,060,619 A | 5/2000 | O'Lenick, Jr. | |
| 7,056,542 B1 | 6/2006 | Bridger et al. | |
| 2009/0200511 A1 | 8/2009 | Allen et al. | |

FOREIGN PATENT DOCUMENTS

| | | |
|---|---|---|
| EP | 0 188 318 | 7/1986 |
| EP | 0 098 663 | 11/1987 |
| EP | 0 258 749 | 3/1988 |
| EP | 1 378 502 | 1/2004 |
| WO | 01/54512 | 8/2001 |
| WO | 2008/033023 | 3/2008 |
| WO | 2008/068763 | 6/2008 |
| WO | 2009/001064 | 12/2008 |

OTHER PUBLICATIONS

International Search Report and Written Opinion dated Nov. 25, 2011 in corresponding PCT/US2010/049242 filed Sep. 17, 2010.
Selmair et al., "Baking Performance of Synthetic Glycolipids in Comparison to Commercial Surfactants," 2008, Journal of Agricultural and Food Chemistry, vol. 56, 6691-6700.
Murphy et al., "The detection and determination of synthetic emulsifiers in foods," 1969, Journal of Food Technology, vol. 4, 227-234.
Selmair et al. "Molecular Structure and Baking Performance of Individual Glycolipid Classes from Lecithins," 2009, Journal of Agricultural and Food Chemistry, vol. 57, 5597-5609.
Seibel et al., "Die Verwendung von Emulgatoren bei Hefefeingeback," 1970, Brot und Geback, 10, 196-200, no English translation available.
Stauffer, "Surface Active: What are emulsifiers and dough conditioners? How do they retard staling, boost aeration, strengthen doughs and even help replace fats and bromates?," 1993, Baking and Snack, 31-32, 36.
Diazald Kit information, Aldrich Chemical Company, Inc., Milwaukee, WI.
PURASORB L Product Data, May 20, 2008, www.purabiomaterials.
Zielinski, "Sythesis and Composition of Food-Grade Emulsifiers," Food Emulsifiers and Their Applications, Chapter Two, Edited by Hasenhuettl and Hartel, Chapman & Hall, International Thomson Publishing, pp. 11-38.
Hasenhuettl, "Synthesis and Commercial Preparation of Food Emulsifiers," Food Emulsifiers and Their Applications, Chapter 2, Second Edition, Edited by Hasenhuettl and Hartel, Springer, pp. 11-37.
Kovacs et al., "Use of Pseudocereals for Pasta Production 1. Use of Quinoa and Its Milling Fractions," Technica Molitoria, 2004, vol. 55, pp. 159-169.
Vu et al., "Oligomer distribution in concentrated lactic acid solutions," 2005, Fluid Phase Equilibria, 236, 125-135.

* cited by examiner

*Primary Examiner* — Paul A Zucker
(74) *Attorney, Agent, or Firm* — Hovey Williams LLP

(57) ABSTRACT

The present invention involves a new synthesis route for the formation of lactylates. The method comprises reacting a dilactide with a compound comprising a hydroxy group. This reaction is preferably carried out in the presence of a cation or other source of alkalinity. Preferred compounds comprising a hydroxy group include any fatty acid and fatty acid alcohol (particularly $C_1$-$C_{26}$ fatty acid chains). Preferred cations include cations of Group I and II metals, with sodium, calcium, and potassium cations being particularly preferred. The inventive reactions proceed much more rapidly than prior art lactylate synthesis reactions, and can be used to form 1-, 2-, 3-, 4-, and 5-lactylates.

35 Claims, 2 Drawing Sheets

LACTYLATE SYNTHESIS METHODS USING DILACTIDES

BACKGROUND OF THE INVENTION

1. Field of the Invention

The present invention is concerned with novel methods of synthesizing lactylates from dilactides.

2. Description of the Prior Art

Lactylates are commonly used in a number of commercial applications. One of the most common applications is as a food additive. For example, several types of lactylates can function as an emulsifier or humectant in food items such as baked goods, cereals, chewing gums, and desserts. Other lactylates find use as a surfactant.

Lactylates have been formed by a variety of processes, with each of these processes having one or more drawbacks. In one prior art process, lactic acid is used to form lactylates, but this process is slow and is limited by lactic acid availability and prices. Various attempts have been made to improve this process, but those have shortcomings as well.

There is a need for new methods of forming lactylates that proceed more rapidly than prior art methods and that do not require the use of lactic acid.

SUMMARY OF THE INVENTION

The present invention is directed towards a method of forming a lactylate. The method comprises reacting a dilactide with a compound comprising an —OH group to form a lactylate. In one embodiment, the reacting is carried out in the presence of a source of alkalinity, such as a cation.

In another embodiment, the invention provides a method of forming a lactylate where the method comprises reacting a reactant mixture to form the lactylate. The reactant mixture consists essentially of a dilactide and a compound comprising an —OH group.

In a further embodiment, an inventive method of forming a lactylate is provided where the method comprises reacting a reactant mixture to form the lactylate. The reactant mixture comprises a dilactide and a compound comprising an —OH group, with the reactant mixture having a molar ratio of lactic acid to dilactide of less than about 0.5:1.

DETAILED DESCRIPTION OF THE PREFERRED EMBODIMENTS

Figure 1:
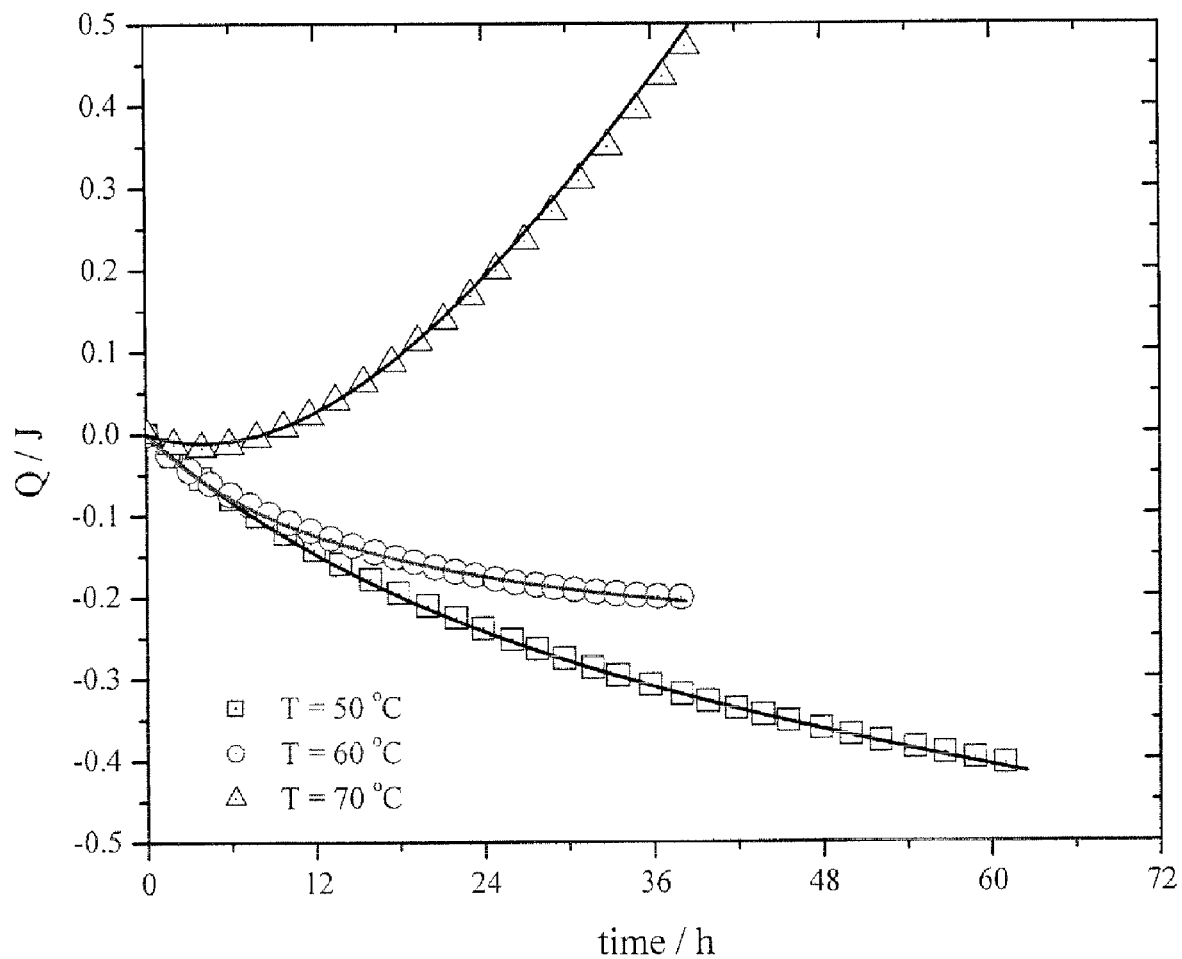
FIG. 1 is a graph showing the static ampoule calorimetric results from Example 11.

The present invention is broadly concerned with a novel synthesis route for forming lactylates. The method comprises reacting a dilactide with a compound comprising an —OH group, preferably in the presence of a cation.

Reactants

The dilactide utilized with the present invention can be any dilactide, including all isomers thereof. Preferred dilactides are represented by the formula

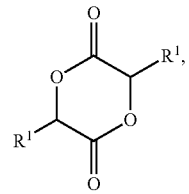

where each $R^1$ is individually selected from the group consisting of —H, substituted (e.g., haloalkyls) and unsubstituted, saturated and unsaturated alkyl groups (preferably from about $C_1$ to about $C_{10}$ and more preferably from about $C_1$ to about $C_4$), substituted and unsubstituted aromatic groups (preferably from about $C_6$ to about $C_{10}$), halogens, and moieties including S, P, N, and/or Si atoms.

The compound that comprises an —OH group can be an alcohol or a carboxylic acid. The compound is preferably a fatty acid or a fatty acid alcohol.

Preferred such compounds have a formula selected from the group consisting of

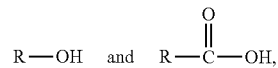

where each R is individually selected from the group consisting of —H, substituted (e.g., haloalkyls) and unsubstituted, saturated and unsaturated alkyl groups (preferably from about $C_1$ to about $C_{26}$ and more preferably from about $C_8$ to about $C_{22}$), substituted and unsubstituted aromatic groups (preferably from about $C_6$ to about $C_{10}$), and silicon-containing groups (e.g., siloxane).

Particularly preferred compounds having an —OH group are selected from the group consisting of stearic acid, palmitic acid, behenic acid, oleic acid, capric acid, caprylic acid, isostearic acid, lauric acid, myristic acid, glycerine, propylene glycol, monoglycerides (e.g., 1-monostearin, 2-monostearin, 1-monopaimitin), diglycerides (e.g., 1-stearic, 3-palmitic diglyceride; 1,3-distearin; 1,2-distearin), and propylene glycol monoester.

In a preferred embodiment, a source of alkalinity is present during the reaction, preferably in the form of a cation. Any cation is acceptable, but preferred cations are cations of Group I, II, and/or III metals. Particularly preferred cations are those of sodium, potassium, calcium, magnesium, lithium, aluminum, and/or ammonium.

The cation can be introduced into the reaction by any known introduction methods. For example, a source of the cation can be introduced into the reaction. Suitable sources of the foregoing cations include Group I and II salts, including salts of stearic acid, palmitic acid, behenic acid, oleic acid, capric acid, caprylic acid, isostearic acid, lauric acid, and/or myristic acid. Specific examples include those selected from the group consisting of sodium stearate, potassium stearate, calcium stearate, sodium palmitate, potassium palmitate, calcium palmitate, sodium behenate, potassium behenate, calcium behenate, sodium oleate, potassium oleate, calcium oleate, sodium caprate, potassium caprate, calcium caprate, sodium isostearate, potassium isostearate, calcium isostearate, sodium caprylate, potassium caprylate, calcium caprylate, sodium laurate, potassium laurate, calcium laurate, sodium myristate, potassium myristate, calcium myristate, aluminum stearate, sodium hydroxide, calcium hydroxide, and tetramethylammonium hydroxide. Alternatively, the cation can be generated in situ prior to and/or during the reacting of the dilactide with the compound comprising an —OH, as described in more detail below.

It is preferred that lactic acid (monomeric, oligomeric, or polymeric) is not among the reactants. More specifically, the molar ratio of lactic acid to dilactide should be less than about 0.5:1, preferably less than about 0.2:1, more preferably less than about 0.05:1, and even more preferably about 0:1. Thus, the reaction mixture is most preferably free of lactic acid, and certainly it is preferred that no lactic acid be added to the reaction mixture.

In another embodiment, the reaction mixture is preferably essentially free of fatty acid halides and/or triglycerides (e.g., stearin). More specifically, it is preferred that the weight ratio of any single one of these components to dilactide be less than about 0.1:1, more preferably less than about 0.05:1, and more preferably about 0:1.

In one embodiment, the reaction mixture consists essentially of or even consists of, the dilactide and the compound comprising an —OH group. In another embodiment, the reaction mixture consists essentially of or even consists of, the dilactide, the compound comprising an —OH group, and the cation or cation source.

Lactylate Synthesis Procedure

The inventive reaction involves heating the compound comprising the —OH group in order to melt that compound, if needed or desired. This is typically accomplished by heating to a temperature of from about 20° C. to about 100° C., and preferably from about 30° C. to about 90° C. The time period for this heating is typically from about 10 minutes to about 60 minutes, and preferably from about 15 minutes to about 30 minutes, although it will be appreciated by those skilled in the art that the actual time required will depend upon the total mass of the compound containing the —OH group as well as the heat source's power and efficiency.

If a cation is utilized, the source of the cation can be combined with the compound comprising an —OH group either before, after, or during the melting thereof. Alternatively, the cation can be generated in situ. One exemplary in situ generation method involves introducing sodium hydroxide (in water) into the reaction vessel while maintaining the temperature at from about 90° C. to about 120° C., and preferably from about 100° C. to about 110° C. The introduction of the sodium hydroxide is carried out over a time period of from about 5 minutes to about 9 minutes, and preferably from about 6 minutes to about 8 minutes.

After the compound comprising an —OH group has melted and after the cation has either been generated or the cation source has been mixed with the compound (if a cation is utilized), the dilactide is combined with the compound comprising an —OH and with the cation (again, if utilized). The dilactide addition is preferably carried out at a temperature of from about 100° C. to about 200° C., preferably from about 160° C. to about 185° C., and more preferably about 180° C. The addition rate can be as rapid as desired because the reaction will take place very rapidly, and preferably nearly instantaneously. Thus, all dilactide is preferably added within about 90 minutes. A desirable rate of reaction is from about 0.001 moles to about 0.075 moles of dilactide per kg of charge per minute, and preferably from about 0.005 moles to about 0.015 moles of dilactide per kg charge per minute. At the above temperatures and rates, at least about 50%, preferably at least about 60%, and more preferably from about 70% to about 90% of the dilactide will be converted (on a molar basis) within about 90 minutes.

The molar ratio of dilactide to the compound comprising an —OH group is preferably from about 1:0.25 to about 1:4, more preferably from about 1:0.5 to about 1:2, and even more preferably about 1:1. When a source of alkalinity (e.g., cation) is utilized, the molar ratio of dilactide to the alkalinity source is preferably from about 1:0.001 to about 1:2, more preferably from about 1:0.25 to about 1:1, and even more preferably about 1:0.5. As appreciated by one skilled in the art, this range will be adjusted, depending upon the source selected.

Reaction Product

The above synthesis procedure results in a product mixture that includes lactylates. The product will include a mixture of lactylates, and Table 1 below sets forth percentages of various lactylates that can be obtained. Some of the specific lactylates that can be formed according to the invention include those selected from the group consisting of palmitoyl-n-lactylate, stearoyl-n-lactylate, behenoyl-n-lactylate, oleoyl-n-lactylate, caproyl-n-lactylate, capryloyl-n-lactylate, lauroyl-n-lactylate, myristoyl-n-lactylate, and mixtures thereof, where each n is individually selected from the group consisting of 1, 2, 3, 4, and 5. It will be appreciated that the lactylate generated will depend upon the R group on the compound comprising an —OH. That is, the fatty acids, blend of fatty acids, alcohols, and/or blends of alcohols utilized will impact which lactylates are generated. For most food applications, 2-lactylates give the best properties, and it will be appreciated that the inventive method yields higher concentrations of 2-lactylates within a similar time frame as compared to the prior art.

TABLE 1[A]

| LACTYLATES | BROADEST RANGE | MORE PREFERRED | MOST PREFERRED |
|---|---|---|---|
| 1-lactylates | at least about 10% | from about 20% to about 70% | from about 40% to about 50% |
| 2-lactylates | at least about 0.01% | from about 5% to about 25% | from about 10% to about 20% |
| 3-lactylates | at least about 0.01% | from about 0.1% to about 15% | from about 1% to about 10% |
| 4-lactylates | at least about 0.01% | from about 0.1% to about 10% | from about 0.1% to about 5% |
| 5-lactylates | at least about 0.01% | from about 0.1% to about 10% | from about 0.1% to about 5% |

[A]Percentages are based upon the total area percent of lactylate species and unreacted starting materials.

The lactylates prepared according to the invention can be used in a number of products, including foods, cosmetics, shampoos, and cleaning products.

EXAMPLES

The following examples set forth preferred methods in accordance with the invention. It is to be understood, however, that these examples are provided by way of illustration and nothing therein should be taken as a limitation upon the overall scope of the invention.

1. Materials
   (a) 100% Lactic acid; liquid and contained monomeric lactic acid; linear polymeric acid where n=2 or more; approximately 5.5% water of esterification; obtained from Purac, Blair, Nebr.
   (b) L-lactide, also known as (S,S)-lactide, a dilactide where both R' groups are —CH$_3$; obtained from Purac.
   (c) Sodium Hydroxide: 50% (weight) in water; obtained from K A Steel. Chemicals Inc., Chicago, Ill.

(d) Calcium Hydroxide: anhydrous powder; obtained from Mississippi Lime, Kansas City, Mo.

(e) Stearic acid: composed of 10% palmitic acid and 90% stearic acid, obtained from PMC Group, Memphis, Tenn.

(f) Sodium Stearate: composed of 55% palmitic acid and 45% stearic acid, obtained from HallStar, Chicago, Ill.

(g) Potassium Stearate: composed of 55% palmitic acid and 45% stearic acid, obtained from HallStar, Chicago, Ill.

(h) Aluminum stearate: tech. grade, also known as aluminum tristearate; fatty acid portion composed of 25% palmitic acid and 63% stearic acid; aluminum has +3 charge; obtained from Alfa Aesar, Ward Hill, Mass.

(i) Tetramethylammonium hydroxide: 25 weight % in water; obtained from Aldrich, Milwaukee, Wis.

(j) Oleic acid (79%), low titer white food grade: minor components are palmitic acid (4%), stearic acid (2%), and linoleic acid (11%); obtained from Chemical Associates of Illinois, Inc., Copley, Ohio.

(k) Capric Acid (99%); obtained from Acme Hardesty Co., Blue Bell, Pa.

(l) Laurie Acid (99%); obtained from Acme Hardesty Co., Blue Bell, Pa.

(m) Hexanes (OmniSolv high purity solvent); obtained from EMD Chemicals, Gibbstown, N.J.

2. Nomenclature (a) Palmitoyl-n-lactylate, where n=1, 2, 3, etc; palmitic acid esterified to lactic acid or linear polymerized lactic acid group, where n denotes number of lactic acid molecules.

(b) Stearoyl-n-lactylate, where n=1, 2, 3, etc.; stearic acid esterified to lactic acid or linear polymerized lactic acid group, where n denotes number of lactic acid molecules.

(c) Dilactic acid; linear dimer of lactic acid, typically formed from either esterification of two lactic acid molecules or hydrolysis of dilactide (d) t=0 when a raw material was added to either —OH or —COOH compound, or mixture of that compound with the cation.

3. GC-FID Procedure

All lactylate profiles were determined by the following procedure. First, 1.00±0.02 g of the sample was placed in a beaker along with 20 mL of ethyl ether and a stir bar. The beaker was covered with a watch glass, followed by stirring and heating at a temperature of 30-35° C. until the sample dissolved. Next, 2.00±0.05 g of Rexyn 101H (Fisher Scientific, Pittsburgh, Pa.) was added to the sample while stirring. Stirring speed was increased as the solution turned from opaque to clear. In instances where the solution didn't become clear in 5 minutes, more Rexyn was added in 0.5 g increments until the solution became clear.

The stirrer was turned off, and the resin allowed to settle to the bottom of the beaker for 1-2 minutes. Next, 2-mL portions of the ether supernatant were pipetted into a vial. Using a Pasteur pipet, 2 mL of diazomethane (prepared from Diazald®, obtained from Aldrich, Milwaukee, Wis., and following the Aldrich's Diazald® Kit procedure) were added to the vial. If the solution of a particular sample did not retain a slight yellow color for at least 30 seconds, more diazomethane was added drop wise until the solution maintained a slight yellow color for at least 30 seconds.

The vial was heated at 35-40° C. until the ether was evaporated, after which 10 mL of methylene chloride were added to the vial, which was then capped and mixed. Next, 1.5 mL of the solution was transferred from the vial to a sample vial that was capped and placed in the autosampler of a Varian 3800 GC system equipped as follows: autosampler, injector, programmable column oven, flame ionization detector (FID), and data handler. The GC column was a Supelco Equity™-1 (15 m×0.53 mm×1.5 μm film).

The GC system had the following settings: injector temperature—300° C.; temperature ramp rate—10° C./min. for 30 min.; detector temperature—300° C.; make up flow—35 mL/min.; hydrogen flow—30 mL/min.; air flow—300 mL/min.; initial S/N ratio—50; initial peak width—4 sec.; initial tangent height—25%; initial peak area reject—3,000; helium flow rate—8.0 mL/min.; pulse psi—14.0; pulse duration—0.20 minutes; and injection volume—1.04

4. Calcium Content Determination

Calcium levels in lactylate products were determined by the following procedure. An empty, clean crucible was heated with a Bunsen burner for sufficient time to ensure complete dehydration. The crucible was placed in a desiccator for 15 minutes in order to allow it to reach thermal equilibrium. The crucible was weighed, and then 1 to 1.5 g of the test sample was placed in the crucible. The sample was heated using a propane torch for 20 minutes in order to drive off all combustible material and ensure complete sample oxidation. The crucible was returned to the desiccator for 15 minutes in order to reach thermal equilibrium. The sample was then reweighed. The calcium percentage was calculated from the percent calcium oxide using the following equation:

$$\frac{0.7147 \times (\text{Crucible wt. after ashing} - \text{Empty crucible wt.}) \times 100}{\text{Sample Weight}}$$

Each test was run in triplicate, and the averages were reported for the reaction products.

5. Sodium Cation Content Determination

Sodium levels in lactylate products were determined using a Mettler DL55 Autotitrator. The settings are shown in the table below.

| Entry Type | Weight |
|---|---|
| Lower Limit (g) | 1.98 |
| Upper Limit (g) | 2.02 |
| Molar Mass M | 23.0 |
| Equivalent number z | 1 |
| Titration Stand | Stand 1 |
| Temperature Sensor | Manual |
| Stir | |
| Speed (%) | 40 |
| Time (s) | 40 |
| EP Titration | |
| Titrant/Sensor | |
| Titrant | HCl |
| Concentration (mol/L) | 0.25 |
| Sensor | DG115 |
| Unit of measurement | pH |
| Predispensing | to volume |
| Volume (mL) | 10 |
| Wait Time (s) | 5 |
| Titrant Addition | Dynamic |
| dE (set) (mV) | 8.0 |
| dV (min) (mL) | 0.02 |
| dV (Max) (mL) | 0.1 |
| dE (mV) | 0.5 |
| dt (s) | 2.0 |
| t(min) (s) | 2.0 |
| t(max) (s) | 20.0 |
| End Point | EP absolute |

-continued

| Entry Type | Weight |
|---|---|
| Potential (mV, pH, . . .) Tendency | 3.8 |
| Tendency Termination | Negative |
| Maximum volume (mL) | 25.0 |
| Delay (s) | 0 |
| Calculation | |
| Formula | R = Q*C/m |
| Constant | C = M/(10*z) |
| Decimal places | 2 |
| Result Unit | % |
| Result Name | Cation as Na+ |
| Statistics | Yes |
| Report | |
| Output | Computer |
| Results | Yes |
| All Results | Yes |
| Raw Results | Yes |
| Table of Measured Values | Yes |
| Sample Data | Yes |
| E-V Curve | Yes |
| dE/dV - V Curve | Yes |
| d2E/DV2 - V Curve | Yes |
| log dE/dV - V Curve | Yes |
| E - t Curve | Yes |
| V - t Curve | Yes |
| dV/dT - t Curve | Yes |

Each test was run in triplicate, and the averages were reported for the reaction products.

6. Potassium Cation Content Determination

The same procedure was followed to determine the potassium content as was followed to determine the sodium content (Part 5 above), except that the molar mass M was changed from 23 (atomic weight of sodium) to 39 (atomic weight of potassium).

7. Tetramethylammonium Cation Determination

A Mettler DL55 Autotitrator was used in this procedure to determine tetramethylammonium cation levels. The settings were the same as those shown in the table of Part 5 above except for the following differences:

| Molar Mass M | 74.14 |
|---|---|
| Speed (%) | 60 |
| Time (s) | 20 |
| Volume (mL) | 5.0 |
| Result Name | Cation as N(CH$_3$)$_4$ |

Each test was run in triplicate, and the averages were reported for the reaction products.

8. Acid Value Determination

Acid values were determined by the following procedure. The sample was weighed into a flask based upon the following table:

| EXPECTED ACID VALUE[A] | WEIGHT (GRAMS) |
|---|---|
| greater than 250 | 0.25 |
| 190-250 | 0.5 |
| 100-190 | 0.75 |
| 40-100 | 1 |
| 10-40 | 1.5 |
| 5-10 | 10 |
| 1-5 | 15 |
| less than 1 | 20 |

[A]The weight selected for the Examples below was the above weight that corresponds to the Acid Value obtained in each Example.

If the sample weighed less than 15 g, 25 ml of reagent alcohol were added. If the sample weighed 15 g or more, 50 ml of reagent alcohol were added. Either way, the weighed sample was placed in the alcohol, and heated and agitated until completely dissolved. A few drops of a mixed indicator solution (Nile blue and phenolphthalein) were added. The sample was allowed to cool to just above room temperature, while ensuring that the sample remained in solution (reheating slightly, if necessary). The solution was titrated rapidly and with agitation, using 0.1N KOH solution until a stable pink endpoint was reached. The acid value is the number of milligrams of potassium hydroxide necessary to neutralize the titratable acids in a sample. The acid value was calculated as:

$$\text{mg KOH per gram of sample} = \frac{\text{ml of Titrant} \times \text{Normality} \times 56.1}{\text{Sample Weight}}$$

Each test was run in triplicate, and the averages were reported for the reaction products.

9. Ester Value Determination

The ester value was determined by the following procedure. The free acid present in a sample weighing 1±0.02 g and in a flask was neutralized with KOH following the Acid Value Determination procedure described above. Next, 10 ml of 0.5N methanolic potassium hydroxide was metered into the sample. A stir bar was added to the solution. The flask was placed on a hot plate and attached to a condenser followed by refluxing for 1 hour in order to ensure complete saponification of the sample. The sample was then cooled to slightly warmer than room temperature and back-titrated with 0.1N HCl to a stable, blue end-point, while ensuring that the sample remained in solution (e.g., through slight heating) throughout the titration. A blank sample was titrated under the same conditions. The ester value was calculated as follows:

$$\frac{56.1 \times N(\text{HCl } Soln) \times (\text{Titration of blank} - \text{Titration of sample})}{\text{Sample Weight}}$$

Each test was run in triplicate, and the averages were reported for the reaction products.

10. Recoverable Lactic Acid

The percent recoverable lactic acid in lactylate products was calculated from the sodium, calcium, or potassium percent, acid value (AV), and ester value (EV), all determined as described above.

For calcium stearoyl lactylates, the recoverable lactic acid was calculated as follows:

%LA=[(Ca$^{2+}$*7.0242)+(AV*0.23513)+(EV*0.22021)]−46.452

For sodium stearoyl lactylates, the recoverable lactic acid was calculated as follows:

%LA=[(Na$^+$*6.1825)+(AV*0.2353)+(EV*0.22021)]−46.452

For potassium stearoyl lactylates, aluminum stearoyl lactylates, N(C$_{1-33}$)$_4$ stearoyl lactylates, oleyl lactylates, and capric-lauric lactylates, the recoverable lactic acid was calculated as described below. The derivation for the total recoverable lactic acid treated the lactylate product as if it were manufactured by the prior art. The rationale used and calculations carried out were as follows:

The total initial mass, $m_0$, is given by the following mass balance equation:

$$m_0 = m_{FA} m_{LA} m_{M(OH)_n} m_{H_2O, neutralization} \quad \text{equation 1}$$

where:
m is the mass of fatty acid charged into the reactor;
$m_{LA}$ is the mass of lactic acid charged into the reactor;
$m_{M(OH)_n}$ is the mass of the hydroxide compound charged into the reactor; and
$m_{H2O, neutralization}$ is the mass of water produced in the neutralization process.

$m_{H2O, neutralization}$ is related to the mass of the hydroxide compound charged in the reactor according to the stoichiometry of the neutralization reaction:

$$RCO_2H + OH^- \rightarrow RCO_2^- + H_2O$$

Therefore, the total initial mass was rewritten as:

$$m_0 = m_{FA} + m_{LA} + m_{M(OH)_n} - \frac{m_{M(OH)_n} \cdot n \cdot FW_{H_2O}}{FW_{M(OH)_n}} \quad \text{equation 2}$$

The total amount of acidic species, $H_0$, present at the start of the reaction is dependent on the amount of fatty acid and lactic acid charged and the degree of neutralization as follows:

$$H_0 = \frac{m_{FA}}{FW_{FA}} + \frac{m_{LA}}{FW_{LA}} - n\frac{m_{M(OH)_2}}{FW_{m(OH)_n}} \quad \text{equation 3}$$

The acid value is related to the amount of acidic species present in the final product. The amount of acidic species will decrease as the ester species are produced:

$$RCO_2H + R'OH \rightarrow RCO_2R' + H_2O$$

Using the stoichiometry of the esterification reaction, the amount of acidic species was expressed in terms of the measured acid value by the following relationship:

$$AV = \frac{H_0 - \frac{m_{H_2O, esterification}}{FW_{H_2O}}}{m_0 - m_{H_2O, esterification}} \cdot FW_{KOH} \cdot 1000 \quad \text{equation 4}$$

Likewise, the measured ester value depends upon the amount of water produced as governed by the stoichiometry of the esterification reaction:

$$EV = \frac{\frac{m_{H_2O, esterification}}{FW_{H_2O}}}{m_0 - m_{H_2O, esterification}} \cdot FW_{KOH} \cdot 1000 \quad \text{equation 5}$$

The percentage cation present depends upon the amount of base charged and the mass of water lost:

$$\%M = \frac{\frac{m_{M(OH)_n}}{FW_{M(OH)_n}} \cdot FW_M}{m_0 - m_{H_2O, esterification}} \cdot 100 \quad \text{equation 6}$$

Equations 2-6 are a system of linear equations consisting of six unknown variables. As the number of unknowns exceeds the number of equations, one variable will be arbitrary. Therefore, one can choose to set the total initial mass to any value desired. Accordingly, the equations were rewritten in vector matrix form (A·x=b) as follows:

$$\begin{bmatrix} 1 & 1 & 1 - \frac{n \cdot FW_{H_2O}}{FW_{M(OH)_n}} & 0 & 0 \\ \frac{1}{FW_{FA}} & \frac{1}{FW_{LA}} & -\frac{n}{FW_{M(OH)_n}} & -1 & 0 \\ 0 & 0 & 0 & 1 & \frac{AV}{FW_{KOH} \cdot 1000} - \frac{1}{FW_{H_2O}} \\ 0 & 0 & 0 & 0 & \frac{EV}{FW_{KOH} \cdot 1000} + \frac{1}{FW_{H_2O}} \\ 0 & 0 & \frac{FW_M}{FW_{M(OH)_n}} & 0 & \frac{\%M}{100} \end{bmatrix}$$

$$\begin{bmatrix} m_{FA} \\ m_{LA} \\ m_{M(OH)_n} \\ H_0 \\ m_{H_2O, esterification} \end{bmatrix} = \begin{bmatrix} m_0 \\ 0 \\ \frac{AV \cdot m_0}{FW_{KOH} \cdot 1000} \\ \frac{EV \cdot m_0}{FW_{KOH} \cdot 1000} \\ \frac{\%M \cdot m_0}{100} \end{bmatrix}$$

The above equation was then solved by multiplying both sides by the inverse of the 5×5 matrix (i.e., x=A$^{-1}$·b). The solution gave the relative masses of fatty acid, lactic acid, and hydroxide compound charged into the reactor, along with the initial amount of acidic species and mass of water produced from the esterification reaction. Once the mass of lactic acid and water of esterification were known, the percent lactic acid was calculated using the following equation:

$$\%LA = \frac{m_{LA}}{m_0 - m_{H_2O, esterification}} \cdot 100 \quad \text{equation 7}$$

11. Control Reaction—Lactylate Formation Using 100% Lactic Acid

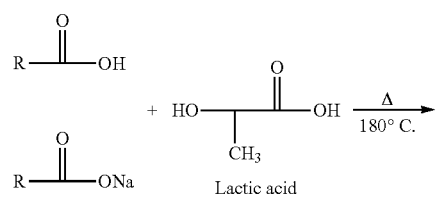

In this procedure, 187.26 g stearic acid and 193.08 g sodium stearate were added to a 4-necked, 1,000-mL, round bottom flask equipped with an overhead stirrer (PTFE paddle on a glass rod and Ace Glass trubore) through the center neck.

The side necks were topped with a thermometer (−10 to 300° C.), nitrogen sparge line (type "A" glass frit on angled glass tube), and an addition funnel with equilibrating side arm. A heating mantle attached to a rheostat was used to heat the flask. Once the stearic acid was melted (~70° C.), the nitrogen sparge was set to 400 mL/min.

Next, 119.66 g of 100% lactic acid were added to the addition funnel. When the reaction temperature reached 180° C., the lactic acid was charged into the reaction (1 mol lactic acid:1 mol stearic acid:0.5 mol Na). Addition was complete at t=10 min. 50 sec., and the reaction temperature fluctuated between 173-182° C. During and after the addition, a graduated pipet was used to withdraw small samples (2-5 mL each) to determine reaction composition over time. The small samples were transferred to 20-mL vials and allowed to cool on the bench.

The heat was turned off at t=28 min. The heating mantle was removed, and the mixture cooled down to between 80-100° C. At t=1 hour, the mixture was poured onto a metal sheet to solidify. The resulting product was an off-white, waxy solid with a tacky surface, and it possessed the following properties:
  (a) QC data: 170.77 Acid Value, 55.53 Ester Value, 3.07% sodium, and 24.32% total recoverable lactic acid; and
  (b) GC-FID: 3.63% lactic acid, 0.11% dilactic acid, 1.32% L-lactide, 21.33% palmitic, 52.83% stearic, 4.78% palmitoyl-1-lactylate, 12.16% stearoyl-1-lactylate, 0.75% palmitoyl-2-lactylate, 1.67% stearoyl-2-lactylate, 0.11% palmitoyl-3-lactylate, and 0.20% stearoyl-3-lactylate.

Using 100% lactic acid required a longer reaction time to achieve the expected lactylate profile as compared to the inventive reactions described below.

Example 1

Commercial Sodium Stearate and Slow Addition of L-Lactide

In this Example, 395.47 g stearic acid and 426.30 g sodium stearate were added to a 4-necked, 2,000 mL round bottom flask equipped with an overhead stirrer (PTFE paddle on a glass rod and Ace Glass trubore) through the center neck. One side neck was topped with a thermometer (−10 to 300° C.), and a second side neck was topped with a nitrogen sparge line (type "A" glass frit on angled glass tube).

A heating mantle attached to a rheostat was used to heat the flask. Once the stearic acid was melted (~70° C.), the nitrogen sparge was set to 400 mL/min. The reaction at this point was a suspension of particles in liquid.

The third side arm was topped with an addition funnel with equilibrating side arm wrapped in silicone heating tapes. The tapes were attached to an analog heat controller. Next, 202.12 g L-lactide was added to the addition funnel and allowed to melt.

When the reaction temperature reached 179° C., the L-lactide was slowly added to the reaction (0.56 mol L-lactide:1 mol fatty acid:0.58 mol sodium). The addition was complete by t=1 hour 13 min., and the reaction temperature was maintained at 180° C.

During and after the addition, a graduated pipet was used to withdraw small (2-5 mL each) samples to determine reaction composition over time. The small samples were transferred to 20 mL vials and allowed to cool on the bench.

The heat was turned off at t=1 hour 44 min. The heating mantle was removed, and the mixture cooled to between 80-100° C. The mixture was poured onto a metal sheet to solidify.

The resulting product was a shiny, brittle, orange-brown colored solid with caramel odor.

The product had the following properties:
  (a) QC data: 90.39 Acid Value; 141.66 Ester Value; 3.14% sodium; and 25.41% total recoverable lactic acid; and
  (b) GC-FID: 13.36% palmitic; 31.83% stearic; 11.42% palmitoyl-1-lactylate; 26.39% stearoyl-1-lactylate; 3.13% palmitoyl-2-lactylate; 7.27% stearoyl-2-lactylate; 0.85% palmitoyl-3-lactylate; 1.84% stearoyl-3-lactylate; 0.46% palmitoyl-4-lactylate; and 0.73% stearoyl-4-lactylate.

The above results show that the inventive reaction proceeds much faster than the prior art reaction. The control reaction set forth above would require at least 5 hours to reach a similar composition as this Example.

Example 2

Lactylate Preparation Using L-Lactide and Commercial Sodium Stearate

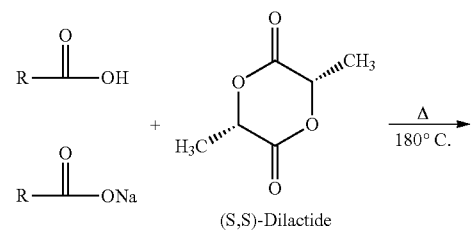

(S,S)-Dilactide

In this procedure, 196.68 g stearic acid and 202.80 g sodium stearate were added to a 4-necked, 1,000-mL, round bottom flask equipped with an overhead stirrer (PTFE paddle on a glass rod and Ace Glass trubore) through the center neck. One side neck was topped with a thermometer (−10 to 300° C.) and a second side neck was topped with a nitrogen sparge line (type "A" glass frit on angled glass tube). The third side arm was topped with an addition funnel with equilibrating side arm wrapped in a silicone heating band. The band was connected to a digital temperature controller. A J-type thermocouple was attached to the controller and tucked between the heating band and the addition funnel. A heating mantle attached to a rheostat was used to heat the flask. Once the stearic acid was melted (~70° C.), the nitrogen sparge was set to 400 mL/min.

Next, 100.52 g L-lactide was added to the addition funnel. The digital controller was set to 120° C. to melt the L-lactide. When the reaction temperature reached 180° C., the L-lactide was charged into the reaction (0.5 mol L-lactide:1 mol stearic acid:0.5 mol Na). The addition was complete by t=2.5 min., and the reaction temperature was maintained at 180° C. During and after the addition, a graduated pipet was used to withdraw small (2-5 mL each) samples to determine reaction composition over time. The small samples were transferred to 20-mL vials and allowed to cool on the bench.

The heat was turned off at t=28 min. The heating mantle was removed, and the mixture cooled down to between 80-100° C. At t=1 hour, the mixture was poured onto a metal sheet to solidify. The resulting product was a shiny, brittle, orange-brown colored solid with a caramel odor. The product had the following properties:

(a) QC data: 93.37 Acid Value, 137.39 Ester Value, 3.07% sodium, and 24.74% total recoverable lactic acid; and (b) GC-FID: 0.63% dilactic acid, 1.42% L-lactide, 19.06% palmitic, 45.83% stearic, 6.78% palmitoyl-1-lactylate, 16.44% stearoyl-1-lactylate, 1.45% palmitoyl-2-lactylate, 3.56% stearoyl-2-lactylate, 0.56% palmitoyl-3-lactylate, 1.27% stearoyl-3-lactylate, 0.32% palmitoyl-4-lactylate, and 0.73% stearoyl-4-lactylate Lactylate formation occurred very rapidly, and much more rapidly than with the control reaction. Furthermore, this Example shows that 180° C. is the preferred temperature for carrying out the reaction.

Example 3

Lactylate Preparation Using L-Lactide and In Situ Sodium Stearate Generation

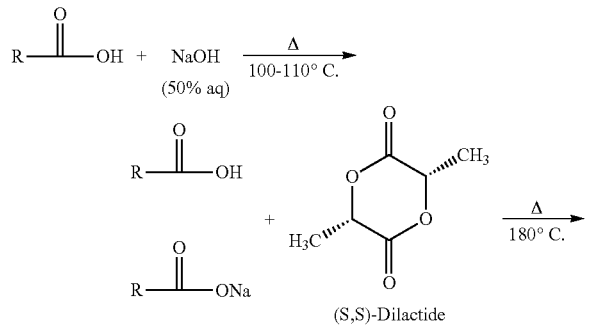

A 4-necked, 1,000-mL round bottom flask equipped with an overhead stirrer (PTFE paddle on a glass rod and Ace Glass trubore) through the center neck and containing 393.36 g stearic acid was utilized in this Example. One side neck was topped with a thermometer (−10 to 300° C.), and a second side neck was topped with a nitrogen sparge line (type "A" glass frit on angled glass tube). The third side arm was left open. A heating mantle attached to a rheostat was used to heat the flask. The stearic acid was melted (~70° C.), and then the nitrogen sparge was set to 700 mL/min.

Next, 55.80 g of a solution of sodium hydroxide in water (50%) was added to the reaction via the third side arm. Addition was complete at t=7 min., and the temperature was maintained between 100-110° C. The resulting mixture was slightly viscous and opaque.

The stir rate was increased to minimize foaming. The reaction was somewhat viscous until 135° C. was reached. The temperature reached 172° C. at t=1 hour 3 min. and resulted in an almost completely transparent mixture.

The third side arm was topped with an S-curved joint and an addition funnel with equilibrating side arm wrapped in a silicone heating band. The band was connected to a digital temperature controller. A J-type thermocouple was attached to the controller and tucked between the heating band and the addition funnel. The digital controller was set to 125° C. to melt the L-lactide. When the temperature reached 95° C., 100.52 g L-lactide was added to the funnel and allowed to melt.

When the reaction temperature reached 180° C., the L-lactide was charged into the reaction at t=3 hour 23 min. (0.5 mol L-lactide:1 mol stearic acid:0.5 mol Na). The addition finished at t=3 hour 25 min. (2 min. reaction charge), and the reaction temperature was maintained at 180° C. During and after the L-lactide addition, a graduated pipet was used to withdraw small (2-5 mL each) samples to determine reaction composition over time. The small samples were transferred to 20-mL vials and allowed to cool on the bench.

The heat was turned off at t=3 hour, 53 min. The heating mantle was removed, and the mixture cooled down to between 80-100° C. At t=4 hour, 24 min., the mixture was poured onto a metal sheet to solidify. The product obtained was a dull, very brittle, orange-brown colored solid with a caramel odor, and it exhibited the following properties:

(a) QC data: 84.66 Acid Value, 139.30 Ester Value, 3.08% sodium, and 23.15% total recoverable lactic acid; and (b) GC-FID: 0.10% dilactic acid, 0.42% L-lactide, 3.23% palmitic, 60.73% stearic, 1.23% palmitoyl-1-lactylate, 24.84% stearoyl-1-lactylate, 0.25% palmitoyl-2-lactylate, 5.43% stearoyl-2-lactylate, 1.53% stearoyl-3-lactylate, and 0.80% stearoyl-4-lactylate The lactylate levels achieved with this Example were slightly higher than those obtained using commercially purchased sodium stearate (Example 2).

Example 4

Lactylate Preparation Using L-Lactide and Commercial Potassium Stearate

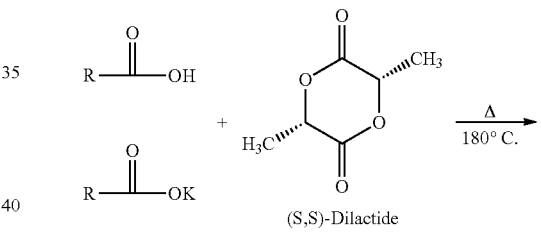

A 4-necked, 1,000-mL round bottom flask equipped with an overhead stirrer (PTFE paddle on a glass rod and Ace Glass trubore) through the center neck was provided, and 196.68 g stearic acid and 214.21 g potassium stearate were added to the flask. One side neck was topped with a thermometer (−10 to 300° C.), and a second side neck was topped with a nitrogen sparge line (type "A" glass frit on angled glass tube).

A heating mantle attached to a rheostat was used to heat the flask. Once the stearic acid was melted (~70° C.), the nitrogen sparge was set to 400 mL/min. The reaction was a mixture of liquid and suspended solids.

The third side arm was topped with an S-curved joint and an addition funnel with equilibrating side arm wrapped in a silicone heating band. The band was connected to a digital temperature controller. A J-type thermocouple was attached to the controller and tucked between the heating band and the addition funnel. The digital controller was set to 125° C. to melt the L-lactide. When the temperature reached 95° C., 100.52 g L-lactide was added to the funnel and allowed to melt. When the reaction temperature reached 180° C., the L-lactide was charged into the reaction (0.5 mol L-lactide:1 mol stearic acid:0.5 mol K). The addition was complete by t=34 sec., and the reaction temperature was maintained at 180° C. During the reaction, the temperature fluctuated between 180-186° C.

During and after the addition, a graduated pipet was used to withdraw small (2-5 mL each) samples to determine reaction composition over time. The small samples were transferred to 20-mL vials and allowed to cool on the bench. The heat was turned off at t=30 min. The heating mantle was removed, and the mixture cooled to between 80-100° C. At t=1 hour, the mixture was poured onto a metal sheet to solidify. The resulting product was a shiny, brittle, coffee-colored solid with a caramel odor. The product analysis showed:
 (a) QC data: 88.95 Acid Value, 119:22 Ester Value, 5.43% potassium, and 20.34% total recoverable lactic acid; and
 (b) GC-FID: 0.16% dilactic acid, 0.68% L-lactide, 15.93% palmitic, 43.92% stearic, 7.39% palmitoyl-1-lactylate, 19.93% stearoyl-1-lactylate, 2.06% palmitoyl-2-lactylate, 4.87% stearoyl-2-lactylate, 0.68% palmitoyl-3-lactylate, 1.57% stearoyl-3-lactylate, 0.32% palmitoyl-4-lactylate, and 0.70% stearoyl-4-lactylate.

The lactylate levels achieved with this method were slightly higher than those achieved using commercial sodium stearate (Example 2). This experiment showed that potassium cations could be used with L-lactides in order to form lactylates. Thus, these results combined with those from Example 2 show that other Group I cations work.

Example 5

Preparation of Lactylates Using L-Lactide and 2-Stage, Calcium Addition

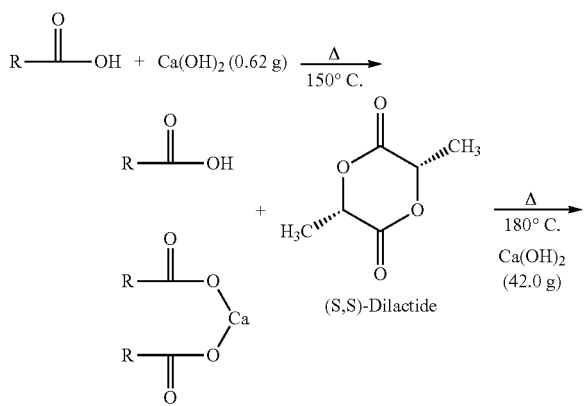

In this procedure, 393.36 g stearic acid was added to a 4-necked, 1,000-mL round bottom flask equipped with an overhead stirrer (PTFE paddle on a glass rod and Ace Glass trubore) through the center neck was used in this Example. One side neck was topped with a thermometer (−10 to 300° C.), and a second side neck was topped with a nitrogen sparge line (type "A" glass frit on angled glass tube). The third side arm was left open. A heating mantle attached to a rheostat was used to heat the flask. Once the stearic acid was melted (—70° C.), the nitrogen sparge was set to 700 mL/rain., and 0.62 g calcium hydroxide was added at 150° C. through the third side arm. The reaction turned hazy and became nearly transparent by t=6 min.

The third side arm was topped with an S-curved joint and an addition funnel with equilibrating side arm wrapped in a silicone heating band. The band was connected to a digital temperature controller. A J-type thermocouple was attached to the controller and tucked between the heating band and the addition funnel. The digital controller was set to 125° C. to melt the L-lactide. When the temperature reached 90° C., 100.52 g L-lactide was added to the funnel and allowed to melt.

During and after the L-lactide addition, a graduated pipet was used to withdraw small (2-5 mL each) samples to determine reaction composition over time. The small samples were transferred to 20-mL vials and allowed to cool on the bench. When the reaction temperature reached 180° C., the L-lactide was charged into the reaction at t=1 hour 11 min. and completed in under 1 min. (0.5 mol L-lactide:1 mol stearic acid:0.4 mol Ca). The reaction fluctuated between 170-179° C.

Addition of 42 g calcium hydroxide was started at t=1 hour 37 min. The addition was complete at t=1 hour 51 min. During the calcium hydroxide addition, the reaction temperature increased to 190° C. and then dropped to 175° C. Water evolved, and the reaction increased in viscosity. At t=3 hour 13 min., the reaction temperature dropped to 164° C., and the reaction mixture became opaque. The heat was turned off at hour 17 min. The heating mantle was removed, and the mixture was cooled to between 80-100° C. At t=3 hour 44 min, the mixture was poured onto a metal sheet to solidify. The product obtained was a shiny, brittle, orange-brown colored solid with a caramel odor. Analysis of the final product showed:
 (a) QC data: 83.63 Acid Value, 99.45 Ester Value, 4.71% calcium, and 28.17% total recoverable lactic acid; and
 (b) GC-FID: 0.58% L-lactide, 2.32% palmitic, 53.75% stearic, 1.53% palmitoyl-1-lactylate, 32.44% stearoyl-1-lactylate, 0.29% palmitoyl-2-lactylate, 6.63% stearoyl-2-lactylate, 1.05% stearoyl-3-lactylate, and 0.16% stearoyl-4-lactylate.

This experiment showed that calcium cations could be used to form lactylates from L-lactides just as potassium and sodium cations could. This Example shows that the reaction works with other divalent cations.

Example 6

Preparation of Lactylates Using L-Lactide and Commercial Aluminum Tristearate

In this procedure, 196.67 g stearic acid and 204.35 g aluminum tristearate were added to a 4-necked, 1,000 mL round bottom flask equipped with an overhead stirrer (PTFE paddle on a glass rod and Ace Glass trubore) through the center neck. One side neck was topped with a thermometer (−10 to 300° C.), and a second side neck was topped with a nitrogen sparge line (type "A" glass frit on angled glass tube). A heating mantle attached to a rheostat was used to heat the flask. Once the stearic acid was melted (~70° C.), the nitrogen sparge was set to 400 mL/min. The reaction was rather viscous and was a mixture of liquid and some solids.

The third side arm was topped with an S-curved joint and an addition funnel with equilibrating side arm wrapped in a silicone heating band. The band was connected to a digital temperature controller. A J-type thermocouple was attached to the controller and tucked between the heating band and the addition funnel. The digital controller was set to 125° C. to melt the L-lactide. When the temperature reached 105° C., 100.52 g L-lactide was added to the funnel and allowed to melt.

When the reaction temperature reached 153° C., the L-lactide was charged into the reaction (0.5 mol L-lactide:1 mol fatty acid:0.167 mol aluminum). The addition was complete by t=1 min. 26 sec. The reaction was heated to 180° C., which took 23 minutes. During the heating stage, the viscosity dropped, and the solids were pulled into solution. The reaction was held between 180-185° C. for 24 minutes.

During and after the addition, a graduated pipet was used to withdraw small (2-5 mL each) samples to determine reaction composition over time. The small samples were transferred to 20 mL vials and allowed to cool on the bench.

The heat was turned off at t=48 min., and the heating mantle was removed. As the mixture cooled, the viscosity increased. At t=1 hour, 6 min. and a temperature between 120-130° C., the mixture was poured onto a metal sheet to solidify. The product obtained was a dull, off-white or pale yellow solid that was not very brittle. Analysis of the final product showed:
  (a) QC data: 150.04 Acid Value; 153.30 Ester Value; 1.62% aluminum; and 30% total recoverable lactic acid; and
  (b) GC-FID: 0.19% dilactic; 3.72% L-lactide; 17.74% palmitic; 70.94% stearic; 0.56% palmitoyl-1-lactylate; 2.09% stearoyl-1-lactylate; 0.10% palmitoyl-2-lactylate; 0.38% stearoyl-2-lactylate; 0.06% palmitoyl-3-lactylate; 0.22% stearoyl-3-lactylate; and 0.16% stearoyl-4-lactylate.

This experiment shows that aluminum cations could be used to form lactylates from L-lactides just as sodium or calcium cations could. Furthermore, this Example shows that the reaction can be carried out successfully with other trivalent cations.

Example 7

Preparation of Lactylates Using L-Lactide and In Situ Generation of Tetramethylammonium Stearate In this Example, 393.36 g stearic acid were added to a 4-necked, 2,000 mL round bottom flask equipped with an overhead stirrer (PTFE paddle on a glass rod and Ace Glass trubore) through the center neck. One side neck was topped with a thermometer (−10 to 300° C.) and a second side neck was topped with a 500-ml addition funnel with equilibrating side arm. The assembly on the third side neck consisted of a "Y"-tube with a thermometer (−10 to 300° C.) on the straight arm and a Barrett distilling receiver (vacuum jacketed, 10 mL capacity) on the bent arm. A compact "thimble" reflux condenser (200 mm, ChemGlass, Vineland, N.J.) was on top of the distilling receiver. The condenser was cooled by flowing tap water through its jacket.

Next, 254.29 g tetramethylammonium hydroxide was added to the addition funnel. A heating mantle attached to a rheostat was used to heat the flask. Once the stearic acid was melted and reached 83° C., the tetramethylammonium hydroxide was added to the flask in less than 3 minutes. Material began to precipitate out of solution. The heat input was turned off, and 650 mL hexanes were added to the reaction via the addition funnel. Once the solvent was in the flask, the addition funnel was replaced with a TEFLON® stopper.

The heat input was turned on in order to slowly raise the temperature of the mixture, which included an opaque liquid and a viscous gel. When the temperature was 79° C., 200 mL of hexanes were added to the flask (for 850 mL of hexanes total).

The reaction vigorously refluxed when the pot temperature reached 85° C., and the liquid portion became translucent. An azeotrope of hexanes and water formed and the "Y" tube thermometer read between 59-60° C. The water collected in the bottom of the Barrett distilling receiver and was drained periodically into a tared, 250-mL Erlenmeyer flask.

To facilitate the gel dissolution process, the heating mantle was removed at one point, and a heat gun was used to soften the gel. Once the gel was solvated, the temperature remained between 61-65° C. while the vapor temperature was 60° C. At t=3 hours, 50 mL of hexanes were added to the flask, bringing the hexanes total to 900 mL.

After 13 hours (16 hours total), the pot temperature was 66° C., and the vapor temperature was 64° C., which is above the boiling point of a hexanes-water azeotrope. During this stage, 176.85 g of water were removed from the reaction as well as 9.25 g of an opaque layer between the water and hexanes layers via the Barrett receiver. With the majority of the water removed, the reaction was foaming less and was transparent.

The distilling receiver's stopcock was opened, and the hexanes were drained out into a 1,000 mL Erlenmeyer flask. As the temperature approached 90° C., the material started to foam again. This step took 3 hours and yielded 775 mL hexanes. The TEFLON® stopper, and the glassware on the third side neck were removed.

The next day, the second side neck was topped with a nitrogen sparge line (type "A" glass frit on angled glass tube). Because the reactor material had solidified, the tube was positioned above the materials' surface and set to 400 mL/min. The heat input was turned on, and the material in the flask was allowed to melt.

The third side arm was topped with an S-curved joint and an addition funnel with equilibrating side arm wrapped in a silicone heating band. The band was connected to a digital temperature controller. A J-type thermocouple was attached to the controller and tucked between the heating band and the addition funnel. The digital controller was set to 125° C. to melt the L-lactide. When the temperature reached 100° C., 100.52 g L-lactide was added to the funnel and allowed to melt.

When the reaction temperature reached 85° C., the L-lactide was charged into the reaction (0.5 mol L-lactide:1 mol fatty acid:0.5 mol tetramethylammonium ion). The addition was complete by t=1 min. 45 sec. Both the viscosity and the foaming reduced after addition. The sparge tube was pushed below the reaction's surface, and the nitrogen sparge maintained at 400 mL/min.

The reaction was heated to 180° C., which took 40 min. The reaction was held between 178-186° C. A bright, yellow-green condensate formed in the S-curve. After the addition, a graduated pipet was used to withdraw small (2-5 mL each) samples to determine reaction composition over time. The small samples were transferred to 20 mL vials and allowed to cool on the bench.

The heat was turned off at t=1 hour 10 min. The heating mantle was removed. At t=1 hour 40 min. and a temperature of 80° C., a small portion of the mixture was poured onto a metal sheet while the remainder were poured into glass jars. The resulting product was a dark brown-red color. The thin film had the consistency of fruit leather. It was pliable under low stress, but would snap apart when sudden stress was applied. The odor was similar to caramel or coffee.

Analysis of the final product showed:
  (a) QC data: 123.12 Acid Value; 93.22 Ester Value; 6.23% tetramethylammonium; and 16.7% total recoverable lactic acid; and
  (b) GC-FID: 0.10% L-lactide; 0.13% trilactic; 7.70% palmitic; 67.84% stearic; 1.65% palmitoyl-1-lactylate; 14.65% stearoyl-1-lactylate; 0.39% palmitoyl-2-lactylate; 0.3.36% stearoyl-2-lactylate; 0.10% palmitoyl-3-lactylate; 0.96% stearoyl-3-lactylate; and 0.22% stearoyl-4-lactylate.

This experiment shows that tetramethylammonium could be used to form lactylates from L-lactides just as sodium and potassium could. Furthermore, this Example shows the reaction can be carried out with other organic-based, complex ions.

Example 8

Preparation of Lactylates Using L-Lactide and In Situ Generation of Capric and Laurie Sodium Salts In this procedure, 120.17 g capric acid and 139.70 g lauric acid were added to a 4-necked, 1,000 mL flask equipped with an overhead stirrer (PTFE paddle on a glass rod and Ace Glass trubore) through the center neck. One side neck was topped with a thermometer (−10 to 300° C.) and a second side neck was topped with a nitrogen sparge line (type "A" glass frit on angled glass tube). The third side arm was left open. A heating mantle attached to a rheostat was used to heat the flask.

Once the fatty acids were melted (~35° C.), the nitrogen sparge was set to 700 mL/min. Sodium hydroxide in water solution was added in an amount of 55.80 g to the reaction via the third side arm. Addition was complete at t=1 min. 50 sec., and the temperature increased from 60° C. to 100° C. The resulting mixture was opaque, slightly viscous and foaming.

When the reaction reached 160° C., the third side arm was topped with an S-curved joint and an addition funnel with equilibrating side arm wrapped in a silicone heating band. The band was connected to a digital temperature controller. A J-type thermocouple was attached to the controller and tucked between the heating band and the addition funnel. The digital controller was set to 125° C. to melt the L-lactide. When the temperature reached 95° C., 100.52 g L-lactide was added to the funnel and allowed to melt.

When the reaction temperature reached 170° C., the L-lactide was charged into the reaction at t=2 hours 55 min. (0.5 mol L-lactide:1 mol fatty acids:0.5 mol sodium). The addition finished at t=2 hours 56 min (55 sec. charge). The temperature continued to climb and was maintained between 180-188° C. for the next 30 minutes.

During and after the L-lactide addition, a graduated pipet was used to withdraw small (2-5 mL each) samples to determine reaction composition over time. The small samples were transferred to 20 mL vials and allowed to cool on the bench.

The heat was turned off at t=3 hours 5 min. The heating mantle was removed, and the mixture cooled to between 80-100° C. At t=3 hours 35 min, the mixture was transferred to an amber glass jar. The final product was initially an amber, orange-yellow, viscous liquid with an acidic-caramel odor. Some solids formed over time. When the sample was mixed, it was pourable.

Analysis of the final product showed the following:
(a) QC data: 125.36 Acid Value; 172.94 Ester Value; 3.86% sodium; and 27.0% total recoverable lactic acid; and
(b) GC-FID: (There were limited standards available for these lactylates. Only those that could be definitively identified are listed. Other species probably exist in the sample); 0.38% dilactic; 1.61% L-lactide; 26.27% capric acid; 31.36% lauric acid; 12.61% capric-1-lactylate; 15.39% lauroyl-1-lactylate; and 3.36% lauroyl-2-lactylate.

This Example showed that capric and lauric fatty acids could be used with L-lactides in order to form lactylates just as stearic acid and palmitic acid could. This experiment further showed that other saturated, organic acids could work in this reaction.

Example 9

Lactylate Preparation Using L-Lactide and In Situ Generation of Oleic Sodium Salts In this procedure, 381.04 g oleic acid were added to a 4-necked, 1,000 mL round bottom flask equipped with an overhead stirrer (PTFE paddle on a glass rod and Ace Glass trubore) through the center neck. One side neck was topped with a thermometer (−10 to 300° C.) and a second side neck was topped with a nitrogen sparge line (type "A" glass fit on angled glass tube). The third side arm was left open. A heating mantle attached to a rheostat was used to heat the flask. Since the fatty acids were liquid at room temperature, the nitrogen sparge was set to 700 mL/min as soon as the reactor was assembled.

Sodium hydroxide in water solution was added in a quantity of 55.80 g to the reaction via the third side arm. Addition was complete at t=50 sec. The resulting mixture was viscous and foaming.

When the reaction reached 173° C., the third side arm was topped with an S-curved joint and an addition funnel with equilibrating side arm wrapped in a silicone heating band. The band was connected to a digital temperature controller. A J-type thermocouple was attached to the controller and tucked between the heating band and the addition funnel. The digital controller was set to 125° C. to melt the L-lactide. When the temperature reached 95° C., 100.52 g L-lactide (0.5 mol L-lactide:1 mol fatty acid:0.5 mol sodium) was added to the funnel and allowed to melt.

When the reaction temperature reached 184° C., the L-lactide was charged into the reaction at t=3 hours 2 min. The addition finished at t=3 hours 4 min. (2 min. 22 sec. charge). The temperature was maintained between 180-185° C. for the next 30 min.

During and after the L-lactide addition, a graduated pipet was used to withdraw small (2-5 mL each) samples to determine the reaction composition over time. The small samples were transferred to 20 mL vials and allowed to cool on the bench.

The heat was turned off at t=3 hours 32 min. The heating mantle was removed, and the mixture cooled to between 80-100° C. At t=4 hours, 2 min, the mixture was transferred to an amber glass jar. The product was an amber, orange-yellow, viscous liquid with an acidic-caramel odor. The analysis of the final product showed the following:
(1) QC data as follows: 83.04 Acid Value; 130.11 Ester Value; 2.9% sodium; and 19.2% total recoverable lactic acid; and
(2) GC-FID: 0.65% dilactic acid; 2.66% palmitic acid; 8.56% linoleic acid; 55.31% oleic acid; 1.33% stearic acid; 1.33% palmitoyl-1-lactylate; 22.67% mono- and diunsaturated octadecenoyl-1-lactylate; 0.47% stearoyl-1-lactylate; 0.24% palmitoyl-2-lactylate; 4.78% mono- and diunsaturated octadecenoyl-2-lactylate; 0.08% stearoyl-2-lactylate; and 1.24% mono- and diunsaturated octadecenoyl-3-lactylate.

This Example showed that oleic acid could be used with L-lactides in order to form lactylates just as stearic, palmitic, lauric, and capric acids could. The experiment also showed that other unsaturated, organic acids could work.

Example 10

Solution Calorimetric Measurements

This procedure was carried out in order to analyze rapid processes associated with uncatalyzed and acid catalyzed reaction pathways. A 0.1 m stock solution of caprylic acid (obtained from Proctor & Gamble, Cincinnati, Ohio) was prepared by mixing 0.7 g of caprylic acid with 49 g of dimethyl sulfoxide ("DMSO," ACS grade; obtained from Amresco, Solon, Ohio). This was referred to as the "uncatalyzed" sample. A second stock solution was prepared by mixing 0.7 g of caprylic acid with 0.5 g phosphoric acid (85%, obtained from EMD Chemical, Gibbstown, N.J.) and 49 g of DMSO. This was referred to as the "acid catalyzed" sample. The concentrations of caprylic acid and phosphoric acid in the second stock solution were both 0.1 m. All weights were accurately determined on an AND HM-200 analytical balance.

The solution calorimetric measurements were determined using the 3456-1 Microsolution calorimeter (TA Instruments) equipped with a stirrer motor set to 200 rpm. Each experimental run was performed in triplicate, and the results averaged. In each run, three 40-4, ampoules, each containing a precisely weighed sample (approximately 26-40 mg) of L-lactide, were loaded into separate microsolution calorimeter solid sample ports: Depending on the experiment, either 5 g of straight DMSO, 0.1 m caprylic acid solution in DMSO solution, 0.1 m caprylic acid/0.1 m phosphoric acid solution in DMSO, or 0.1 m caprylic acid solution in DMSO with an additional 34 mg of concentrated $H_2SO_4$ (obtained from J. T. Baker, New Jersey) were then accurately weighed into a 20-mL glass or Hastelloy reaction vessel. This reaction vessel was then assembled onto the solution calorimeter. The entire solution calorimeter assembly was lowered into the sample side of a TAM III (TA Instruments) 20-mL calorimeter. A reference was prepared by accurately weighing 5 g of DMSO into a second, matching 20-mL glass or Hastelloy reaction vessel and lowered into the reference side of the TAM III calorimeter. The system was allowed to equilibrate to the bath temperature, set to either 50° C., 60° C., or 70° C. prior to initiation of the reaction. Each sample of L-lactide was injected directly into the stirred solvent mixture, and the total observed heat recorded. This procedure was repeated with both aged (i.e., L-lactide that was 6 months old stored at room temperature) and fresh (i.e., stored at 2-8° C.) L-lactide. The results are set forth in Tables 2 (aged L-lactide) and 3 (fresh L-lactide).

TABLE 2

Q (KJ/mole L-lactide)

| SAMPLE | 50° C. | 60° C. | 70° C. |
|---|---|---|---|
| Blank | +12.0 ± 0.1 | +11.66 ± 0.07 | +9.8 ± 0.4 |
| Uncatalyzed | +11.7 ± 0.1 | +11.43 ± 0.08 | +8.7 ± 0.7 |
| Acid Catalyzed | +12.15 ± 0.02 | +11.2 ± 0.4 | +11.1 ± 0.3 |

TABLE 3

Q (KJ/mole L-lactide)

| SAMPLE | 50° C. |
|---|---|
| Blank | +15.47 ± 0.05 |
| Uncatalyzed | +14.98 ± 0.02 |
| Acid Catalyzed | +15.221 ± 0.009 |

The observed heats provide evidence of a reaction between the acid and L-lactide reactants.

The 60° C. catalyzed and 60° C. uncatalyzed samples were also subject to GC-FID Analysis. There was a peak observed at retention time ("RT") 10.8 min. The component level (uncorrected area percent) was: 9% (uncatalyzed at 50° C.); 38% (acid catalyzed at 60° C.); 13% (uncatalyzed at 70° C.); and 37% (acid catalyzed at 70° C.). An octyl-1-lactylate standard was found to elute at RT 11.0 min. Thus, the RT 10.8 min component was structurally similar to octyl-1-lactylate (MS and FT-IR data), but confirmed to be different from octyl-1-lactylate. Octyl-1-lactylate was present in trace amounts in each sample. Thus, it can be concluded that L-lactide reacts with octanoic acid at these temperatures and under these reaction conditions to form lactylates.

Example 11

Static Ampoule Thermokinetic Measurements

This procedure was carried out in order to analyze slower processes associated with uncatalyzed reaction pathways. The reaction samples were prepared by weighing 90 to 100 mg of L-lactide and 5 g of 0.1 m caprylic acid in DMSO solution into a 20-mL Hastelloy reaction vessel. After sealing the reaction vessel, it was lowered into the sample side of a TAM III 20-mL calorimeter. A reference was prepared by weighing 5 g of DMSO into a second, matching 20-mL Hastelloy reaction vessel and lowering into the reference side of the TAM III calorimeter. The system was allowed to equilibrate to the bath temperature, set to either 50° C., 60° C., or 70° C., prior to lowering the reaction vessels into the measurement position. The heat-flow signal for the reaction was collected over a 40- to 60-hour period. This signal was baseline corrected prior to exporting for thermokinetic analysis and calculation of the best-fit line. The results are set forth in Tables 4-6 and FIG. 1.

TABLE 4

Empirical Rate Constants

| RATE CONSTANT | 50° C. | 60° C. | 70° C. |
|---|---|---|---|
| $\log_{10}[k'/(m^{-1}h^{-1})]$ | −2.17 | −2.12 | −2.62 |
| $\log_{10}[k_3/(m^{-1}h^{-1})]$ | −0.27 | 0.12 | 0.26 |
| $\log_{10}[k_4/h]$ | — | −2.48 | −0.66 |

TABLE 5

Enthalpies of Reaction

|  | ΔH' | ΔH$_2$ | ΔH$_3$ |
|---|---|---|---|
| ΔH/(kJ/mol) | +34.2 | −26.5 | −94.6 |

TABLE 6

Apparent Activation Energies and Pre-Exponential Factors

| ASSOCIATED REACTION | $E_a$/(kJ/mol)[A] | ln A |
|---|---|---|
| k' | 10.8 | −2.59 |
| k$_3$ | 57.0 | 19.1 |
| k$_4$ | 398 | 137 |

[A]$E_a$ and ln A for k' calculated using 50° C. and 60° C. data only.

The following calculations were used with FIG. 1 and the above tables:

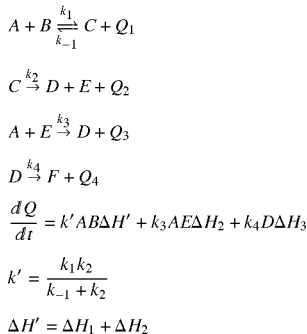

Overall, the results of Examples 10 and 11 show that the dilactide reaction can be carried out under both acid catalyzed and uncatalyzed reaction conditions, as well as using a partially neutralized or "base attack" process as shown in Examples 1-9. This gives more options to the manufacturer to select the best conditions for its particular purpose. Furthermore, the dilactide reaction can be carried out with or without a solvent, and the reaction pathway is fundamentally different from the direct esterification pathway associated with the prior art.

Example 12

Static Ampoule Compatibility Measurements

This experiment was performed to analyze the reactivity of dilactides with alcohols such as monoglycerides and diglycerides. Three samples—two background samples and one reaction sample—were prepared in separate 20-mL stainless steel reaction vessels. The background samples were prepared by transferring 8.84 g of BFP 75 PLM (a 60% mono-diglyceride, obtained from Caravan Ingredients, Dolton, Ill.) and 8.85 g of L-lactide to separate reaction vessels. The reaction sample was prepared by transferring 4.39 g of BFP 75 PLM and 4.53 g of dilactide to a third reaction vessel. After sealing each reaction vessel, the reaction vessels were lowered into one of the channels of a TAM III 20-mL multicalorimeter. The multicalorimeter utilized a permanently mounted reference with a total heat capacity of 57 J/K. The systems were allowed to equilibrate with the bath temperature, set to 130° C., prior to lowering the reaction vessels into the measurement positions. The heat-flow signals for each sample were collected over a 17-hour period. These signals were baseline corrected prior to exportation for analysis.

Figure 2:
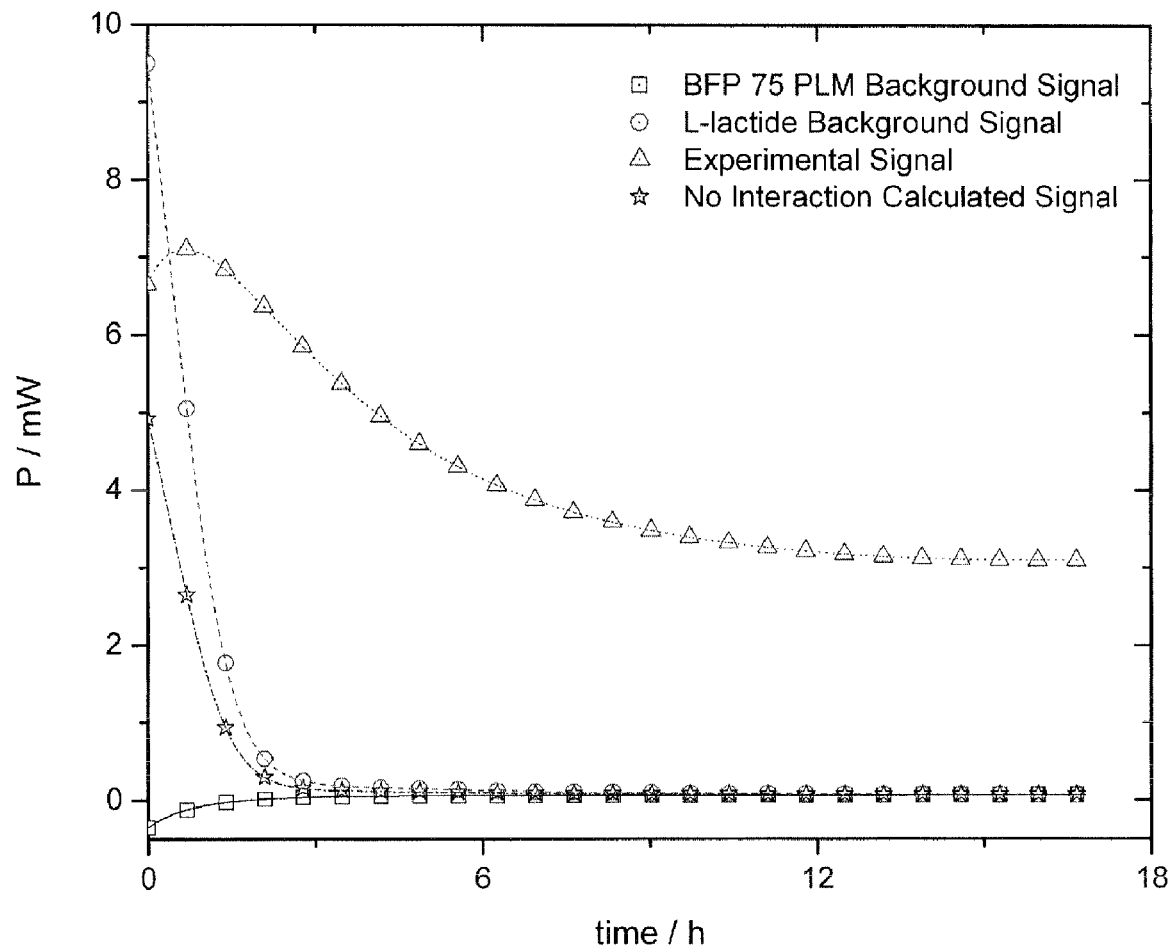
FIG. 2 is a graph showing the power vs. time curves for two background samples and one reaction sample, as described in Example 12.

FIG. 2 shows the power vs. time profiles for the two background samples and the reaction (experimental) signal. According to Hess's Law of heat summation, the expected power signal for a simple blend of the two components displaying no interactions would be given by:

$$P = \sum_{i=1}^{2} f_i P_i$$

where:
$f_i$ is the fraction of the component in the system; and
$P_i$ is the pure power signal associated with the $i^{th}$ component.

This equation was used to calculate a no interaction signal, which is also shown in FIG. 2. As can be clearly seen from the data, the observed signal is significantly more exothermic than the no interaction signal (3.02 mW stronger after about 17 hours). The reaction sample was also analyzed by GC-FID against BFP GLP (lactylated 60% mono-diglyceride, obtained from Caravan Ingredients, Dolton, Ill.). The GC-FID profiles showed that the chemical species signature of the TAM reaction sample was consistent with a commercial lactylated mono-diglyceride. These data demonstrate that L-lactide reacts with mono- and diglycerides, and therefore can be used to make lactylated esters of alcohols including glycerols and glycols.

We claim:

1. A method of forming a lactylate, said method comprising reacting a dilactide with a compound comprising an —OH group to form a lactylate, wherein the molar ratio of dilactide to the compound comprising an —OH group is from about 1:0.25 to about 1:4.

2. The method of claim 1, wherein said compound comprises a —COOH group.

3. The method of claim 1, wherein said reacting is carried out in the presence of a source of alkalinity.

4. The method of claim 1, wherein said reacting is carried out in the presence of a cation.

5. The method of claim 4, wherein said cation is selected from the group consisting of cations of Group I, II, and III metals.

6. The method of claim 4, wherein said cation is selected from the group consisting of cations of sodium, potassium, calcium, magnesium, aluminum, ammonium, and lithium.

7. The method of claim 4, wherein the source of said cation is selected from the group consisting of sodium stearate, potassium stearate, calcium stearate, sodium palmitate, potassium palmitate, calcium palmitate, sodium behenate, potassium behenate, calcium behenate, sodium oleate, potassium oleate, calcium oleate, sodium caprate, potassium caprate, calcium caprate, sodium isostearate, potassium isostearate, calcium isostearate, sodium caprylate, potassium caprylate, calcium caprylate, sodium laurate, potassium laurate, calcium laurate, sodium myristate, potassium myristate, calcium myristate, aluminum stearate, sodium hydroxide, calcium hydroxide, and tetramethylammonium hydroxide.

8. The method of claim 4, further comprising generating said cation in situ prior to, during, or prior to and during, said reacting.

9. The method of claim 1, wherein said compound comprising an —OH group has a formula selected from the group consisting of

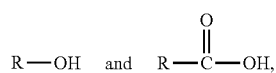

where each R is individually selected from the group consisting of —H, substituted and unsubstituted and saturated and unsaturated alkyl groups, substituted and unsubstituted aromatic groups, and silicon-containing groups.

10. The method of claim 9, wherein said compound is selected from the group consisting of stearic acid, palmitic acid, behenic acid, oleic acid, capric acid, caprylic acid, isostearic acid, lauric acid, myristic acid, glycerine, propylene glycol, monoglycerides, diglycerides, and propylene glycol monoester.

11. The method of claim 1, wherein said dilactide has the formula

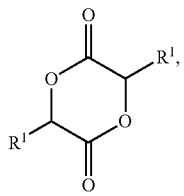

where each $R^1$ is individually selected from the group consisting of —H, substituted and unsubstituted and saturated and unsaturated alkyl groups, substituted and unsubstituted aromatic groups, halogens, and moieties including S, P, N, and/or Si atoms.

12. The method of claim 1, wherein said reacting forms a mixture of lactylates.

13. The method of claim 1, wherein said lactylate is selected from the group consisting of 1-lactylates, 2-lactylates, 3-lactylates, 4-lactylates, 5-lactylates, and mixtures thereof.

14. The method of claim 13, wherein said lactylate is selected from the group consisting of palmitoyl-n-lactylate, stearoyl-n-lactylate, behenoyl-n-lactylate, oleoyl-n-lactylate, caproyl-n-lactylate, capryloyl-n-lactylate, lauroyl-n-lactylate, myristoyl-n-lactylate, and mixtures thereof, where each n is individually selected from the group consisting of 1, 2, 3, 4, and 5.

15. The method of claim 1, wherein said reacting is carried out at a temperature of from about 100° C. to about 200° C.

16. The method of claim 1, wherein said reacting is carried out for a time period of less than about 90 minutes.

17. The method of claim 15, wherein said reacting is carried out for a time period of less than about 90 minutes.

18. A method of forming a lactylate, said method comprising reacting a reactant mixture to form the lactylate, said reactant mixture consisting essentially of a dilactide and a compound comprising an —OH group, and having a molar ratio of lactic acid to dilactide of less than about 0.5:1.

19. The method of claim 18, wherein said compound comprises a —COOH group.

20. The method of claim 18, wherein said reacting is carried out in the presence of a source of alkalinity.

21. The method of claim 18, wherein said reacting is carried out in the presence of a cation.

22. The method of claim 18, wherein said compound comprising an —OH group has a formula selected from the group consisting of

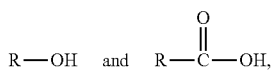

where each R is individually selected from the group consisting of —H, substituted and unsubstituted and saturated and unsaturated alkyl groups, substituted and unsubstituted aromatic groups, and silicon-containing groups.

23. The method of claim 18, wherein said dilactide has the formula

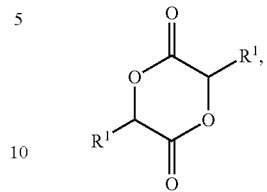

where each $R^1$ is individually selected from the group consisting of —H, substituted and unsubstituted and saturated and unsaturated alkyl groups, substituted and unsubstituted aromatic groups, halogens, and moieties including S, P, N, and/or Si atoms.

24. The method of claim 18, wherein said reacting forms a mixture of lactylates.

25. The method of claim 18, wherein said reacting is carried out at a temperature of from about 100° C. to about 200° C.

26. The method of claim 18, wherein said reacting is carried out for a time period of less than about 90 minutes.

27. A method of forming a lactylate, said method comprising reacting a reactant mixture to form the lactylate, said reactant mixture comprising a dilactide and a compound comprising an —OH group, said reactant mixture having a molar ratio of lactic acid to dilactide of less than about 0.5:1.

28. The method of claim 27, wherein said compound comprises a —COOH group.

29. The method of claim 27, wherein said reacting is carried out in the presence of a source of alkalinity.

30. The method of claim 29, wherein said source of alkalinity is a cation.

31. The method of claim 27, wherein said compound comprising an —OH group has a formula selected from the group consisting of

where each R is individually selected from the group consisting of —H, substituted and unsubstituted and saturated and unsaturated alkyl groups, substituted and unsubstituted aromatic groups, and silicon-containing groups.

32. The method of claim 27, wherein said dilactide has the formula

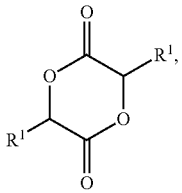

where each $R^1$ is individually selected from the group consisting of —H, substituted and unsubstituted and saturated and unsaturated alkyl groups, substituted and unsubstituted aromatic groups, halogens, and moieties including S, P, N, and/or Si atoms.

33. The method of claim 27, wherein said reacting forms a mixture of lactylates.

34. The method of claim 27, wherein said reacting is carried out at a temperature of from about 100° C. to about 200° C.

35. The method of claim 27, wherein said reacting is carried out for a time period of less than about 90 minutes.

* * * * *